United States Patent
Dextradeur et al.

(10) Patent No.: US 10,828,474 B2
(45) Date of Patent: Nov. 10, 2020

(54) BODILY FLUID DRAINAGE SYSTEM WITH VOLUME LIMITING AND ADJUSTABLE VOLUME CAPACITY FUNCTIONALITY

(71) Applicant: Integra LifeSciences Switzerland Sárl, Le Locle (CH)

(72) Inventors: Alan J. Dextradeur, Franklin, MA (US); Michael A. DeFusco, North Attleboro, MA (US); Alyssa R. Trigger, South Boston, MA (US)

(73) Assignee: Integra LifeSciences Switzerland Sárl, Le Locle (CH)

( * ) Notice: Subject to any disclaimer, the term of this patent is extended or adjusted under 35 U.S.C. 154(b) by 431 days.

(21) Appl. No.: 15/702,283

(22) Filed: Sep. 12, 2017

(65) Prior Publication Data
US 2019/0076630 A1    Mar. 14, 2019

(51) Int. Cl.
*A61M 27/00*    (2006.01)

(52) U.S. Cl.
CPC ....... *A61M 27/006* (2013.01); *A61M 2205/04* (2013.01); *A61M 2205/3382* (2013.01)

(58) Field of Classification Search
CPC ............ A61M 27/006; A61M 2205/04; A61M 2205/3382; A61M 1/0001; A61M 1/0003; A61M 1/0023; A61M 1/0049; A61M 1/005; F16K 17/366; F16L 55/10; F16L 55/1022
See application file for complete search history.

(56) References Cited

U.S. PATENT DOCUMENTS

| | | | | |
|---|---|---|---|---|
| 2,510,356 A | * | 6/1950 | Werts | E21B 34/02 137/454.2 |
| 2,601,304 A | * | 6/1952 | Lanc | F16K 3/184 251/199 |
| 2,927,592 A | * | 3/1960 | Ferre, Sr. | F16K 17/366 137/38 |
| 3,957,050 A | * | 5/1976 | Hines, Jr. | A61M 27/006 604/118 |
| 4,005,724 A | * | 2/1977 | Courtot | F16K 17/366 137/38 |
| 4,089,343 A | * | 5/1978 | Ishida | F16K 17/20 137/484.8 |
| 4,382,449 A | * | 5/1983 | Nelson | F16K 17/36 137/38 |
| 4,430,085 A | | 2/1984 | Ahrens | |
| 4,500,311 A | | 2/1985 | Redmond et al. | |
| 4,565,208 A | * | 1/1986 | Ritchie | F16K 17/366 137/38 |
| 4,595,390 A | | 6/1986 | Hakim et al. | |
| 4,681,559 A | * | 7/1987 | Hooven | A61M 27/006 137/504 |
| 4,905,325 A | | 3/1990 | Colditz | |
| 4,963,135 A | * | 10/1990 | Kerwin | A61M 1/0013 137/205 |
| 5,207,661 A | | 5/1993 | Repschlager | |

(Continued)

*Primary Examiner* — Adam Marcetich
(74) *Attorney, Agent, or Firm* — Cohen & Hildebrand, PLLC

(57) ABSTRACT

An implantable bodily fluid drainage system including a collection vessel and a mechanical volume limiting mechanism for preventing overfill of the collection chamber. The mechanical volume limiting mechanism is not susceptible to malfunction if immersed in the bodily fluid. Moreover, the volume capacity of the fluid collection chamber is adjustable in addition to the overfill prevention functionality.

14 Claims, 10 Drawing Sheets

(56) References Cited

U.S. PATENT DOCUMENTS

| | | | |
|---|---|---|---|
| 5,449,015 A * | 9/1995 | Petkovic | F16K 17/36 137/38 |
| 5,564,464 A | 10/1996 | Pendleton et al. | |
| 5,669,892 A | 9/1997 | Keogh et al. | |
| 5,683,357 A | 11/1997 | Magram | |
| 5,741,237 A * | 4/1998 | Walker | B08B 3/08 134/50 |
| 5,772,607 A | 6/1998 | Magram | |
| 5,782,263 A | 7/1998 | Isaacson, Jr. et al. | |
| 6,095,206 A | 8/2000 | Jones et al. | |
| 6,109,287 A * | 8/2000 | Cole | F16K 17/366 137/38 |
| 6,510,747 B1 * | 1/2003 | Zaiser | F16K 3/34 251/205 |
| 6,997,644 B2 | 2/2006 | Fleeger | |
| 8,221,366 B2 | 7/2012 | Hoffman et al. | |
| 8,292,859 B2 | 10/2012 | Salvadori | |
| 8,322,365 B2 | 12/2012 | Wilson et al. | |
| 8,475,419 B2 | 7/2013 | Eckermann | |
| 8,603,057 B2 | 12/2013 | Hoffman et al. | |
| 8,617,142 B2 | 12/2013 | Wilson et al. | |
| 9,149,615 B2 | 10/2015 | Wilson | |
| 9,205,184 B2 | 12/2015 | Eckermann | |
| 9,498,605 B2 | 11/2016 | Fifolt et al. | |
| 2002/0007157 A1 * | 1/2002 | Azzolini | A61M 39/223 604/247 |
| 2002/0095125 A1 * | 7/2002 | Parker | A61M 1/0019 604/327 |
| 2003/0004495 A1 | 1/2003 | Saul | |
| 2004/0182456 A1 * | 9/2004 | Rousselin | F16K 11/074 137/625.3 |
| 2005/0061764 A1 * | 3/2005 | Tamashiro | B65D 7/04 215/12.1 |
| 2005/0155849 A1 * | 7/2005 | Chang | F16K 17/366 200/61.52 |
| 2005/0247901 A1 * | 11/2005 | Wang | F16K 3/08 251/206 |
| 2006/0090792 A1 * | 5/2006 | Tamian | F16K 17/366 137/38 |
| 2008/0045912 A1 * | 2/2008 | Orwig | A61M 1/0049 604/319 |
| 2008/0060701 A1 * | 3/2008 | Kim | F16K 17/363 137/38 |
| 2009/0054857 A1 | 2/2009 | Eckermann | |
| 2009/0088710 A1 * | 4/2009 | Hoffman | A61M 1/005 604/323 |
| 2010/0175718 A1 | 7/2010 | Kedjierski et al. | |
| 2012/0012186 A1 * | 1/2012 | Tantra | A61M 16/16 137/1 |
| 2012/0226215 A1 * | 9/2012 | Hsu | A61M 27/006 604/9 |
| 2012/0283676 A1 | 11/2012 | Hoffman et al. | |
| 2013/0240549 A1 * | 9/2013 | Beggins | B65D 21/086 220/739 |
| 2014/0155847 A1 * | 6/2014 | Neatrour | A61M 1/0001 604/319 |
| 2014/0194840 A1 | 7/2014 | Eckermann | |
| 2014/0276348 A1 | 9/2014 | Dextradeur | |
| 2015/0011953 A1 * | 1/2015 | Schmidt | A61M 1/0025 604/318 |
| 2015/0273192 A1 * | 10/2015 | Fifolt | A61M 27/00 604/540 |
| 2015/0380190 A1 * | 12/2015 | Solis | H01H 35/141 200/61.45 M |
| 2016/0082232 A1 | 3/2016 | Seaver et al. | |
| 2016/0235951 A1 | 8/2016 | Dextradeur | |
| 2017/0095650 A1 | 4/2017 | Wilson | |
| 2018/0195631 A1 * | 7/2018 | Kane | F16K 3/0254 |

\* cited by examiner

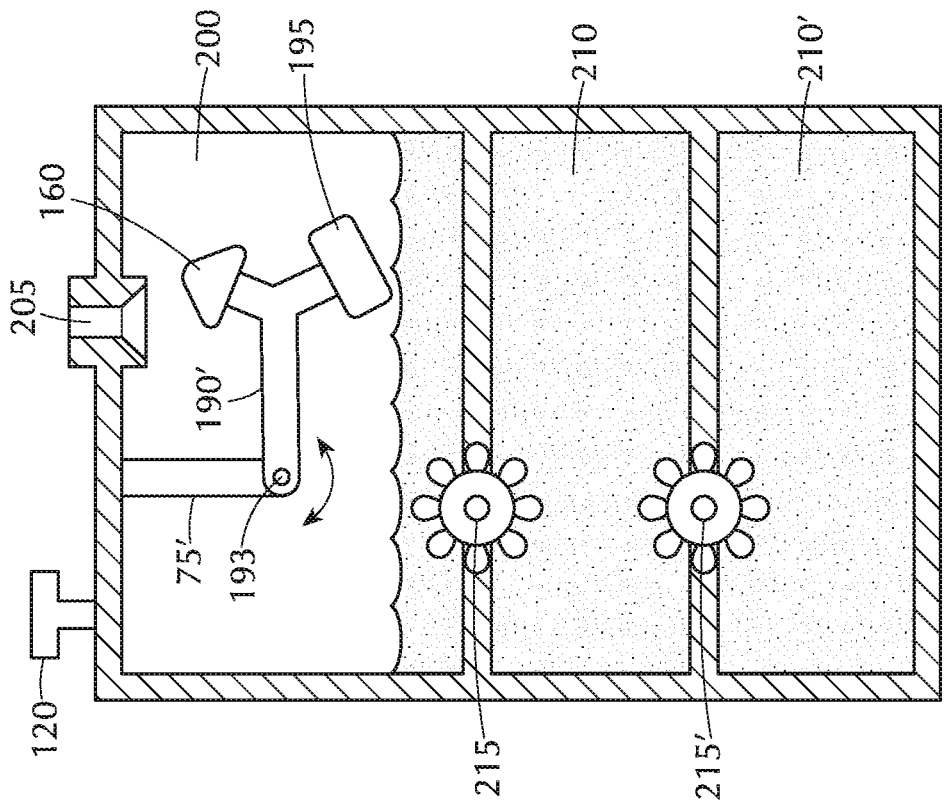
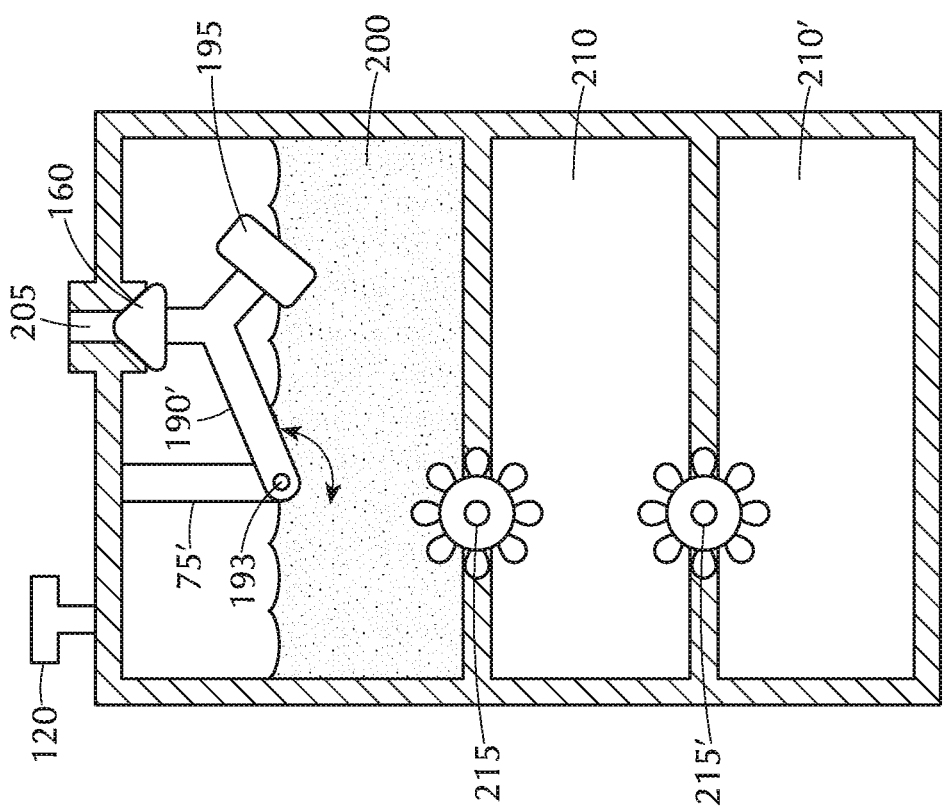

US 10,828,474 B2

BODILY FLUID DRAINAGE SYSTEM WITH VOLUME LIMITING AND ADJUSTABLE VOLUME CAPACITY FUNCTIONALITY

BACKGROUND OF THE INVENTION

Field of the Invention

The present invention relates to a drainage system, in particular, an implantable system for the drainage of a bodily fluid such as cerebrospinal fluid (CSF). More particularly, the invention relates to an improved bodily fluid drainage system with volume limiting and adjustable volume capacity functionality.

Description of Related Art

During treatment for medical disorders it is not uncommon to require the removal of excess fluid from the body. One common use of such bodily drainage systems is in the treatment of hydrocephalus, namely the build-up of CSF that surrounds the brain. Under normal conditions, the rate at which the CSF is produced is substantially equal to the rate at which it is absorbed by the body. Any excess build-up of CSF when this rate is no longer equal results in undesirable increased intracranial pressure (ICP) beyond normal physiological maximum pressure limits. During the treatment of hydrocephalus, a shunt is typically implanted in fluid communication with a ventricle within the brain to allow for drainage of the CSF at a desired rate. Maintaining the proper drainage flow rate is important. On the one hand, too fast a flow rate ("overdrainage") may result in severe headaches or collapse of one or more ventricular cavities within the brain. Whereas, on the other hand, too slow a flow rate ("underdrainage") may result in undesired intracranial pressure resulting in possible brain damage.

The rate of flow or drainage of the CSF is adjustable via a programmable valve having a plurality of different pressure settings. Desirably, such programmable pressure settings are adjustable non-invasively following implantation in the body. This way the pressure setting may be controlled over the duration that the drainage system is implanted in the body should conditions warrant adjustment. For example, commercially available implantable valves sold by Codman & Shurtleff, Inc. including the CODMAN® HAKIM® programmable valve (U.S. Pat. No. 4,595,390) or the CERTAS® programmable valve (U.S. Pat. No. 8,322,365), each herein incorporated by reference in their entirety. In these external drainage systems, CSF is drained from the body into an external collection chamber. External drainage systems drain bodily fluid from the patient through a drainage catheter into an external sterile collection container (e.g., a bag) in which the fluid is collected. Hence, such external drainage system is a "closed" collection system (i.e., wherein the bodily fluid is not exposed to microbes in room air) to prevent infection. Overfilling of the collection container may undesirably leak fluid from the closed collection system resulting in faulty operation of the system upon becoming wet (e.g., if the filter becomes wet from the bodily fluid) and/or possible infection within the drainage system if the fluid becomes exposed to microbes in the room air.

Of course, visual monitoring of the level of bodily fluid collected is one way to prevent such overfilling of the collection container, however, this requires one-on-one monitoring by a medical professional who typically cannot devote such time to only one patient given the number of patients under their care to at any given time. It is therefore desirable to develop an overfill prevention system for a bodily fluid drainage system that does not require continuous visual monitoring by medical personnel.

U.S. Pat. No. 8,221,366 is directed to a volume limiting bodily fluid drainage system comprising a buoyant float hingedly connected with the top of the collection chamber. The buoyant float member has a lumen that is filed with air, gas or other buoyant material. This float member occupies a volume of about 10 ml to about 15 ml within the collection chamber. The collection chamber lumen is configured with a volume about equal to, or slightly larger than the float member volume plus the prescribed volume. The volume of the collection chamber exceeds the combined volumes of the float member and the prescribed volume by about 2 ml to about 10 ml. As a result, this patented float member undesirably takes up a significant volume within the collection chamber leaving only a small proportion of the volume of the collection chamber for fluid to be collected or otherwise requires a very large collection chamber sufficient to accommodate the combined volume required both for the float member and the capacity of fluid to be drained from the patient.

The configuration in U.S. Pat. No. 8,221,366 also disadvantageously requires that the float member be designed at its top portion to include a hollow chimney extension with a pressure equalization hole at the top. Such pressure equalization hole communicates with air inside the float member lumen permitting gases under pressure to flow into or out of the float member lumen through the pressure equalization hole. The pressure equalization hole equalizes pressure differences between the inside and outside of the float member during sterilization under pressure, thereby preventing damage to the float member during sterilization processing. The hollow chimney extension is expressly intended to position the equalization hole sufficiently high up in the collection chamber well above the collected fluid level, thereby preventing the collected fluid (e.g., CSF) from entering the float member lumen under normal operating conditions. Due to the fact that the buoyant float member is filled with air, gas or other buoyant material, it is important to avoid fluid from entering the float chamber lumen which could affect buoyancy and hence proper overfill prevention functionality. Thus, the volume of fluid collectable in the U.S. Pat. No. 8,221,366 apparatus is disadvantageously limited not only by the overall volume of the float member, as discussed in the preceding paragraph, but also by the required hollow chimney design with the hole at the top in which fluid must be prevented from entering. This patented assembly is also limited only to overfill prevention without permitting adjustment of the volume capacity of the collection chamber itself.

It is therefore desirable to develop an improved volume limiting bodily fluid drainage system in which the proportion of volume within the collection chamber taken up by the volume limiting mechanism is minimized and not susceptible to malfunction in the event of exposure to the bodily fluid. Moreover, it is desirable to develop an improved bodily fluid drainage system in which the volume capacity of the fluid collection chamber is adjustable in addition to the overfill prevention functionality.

SUMMARY OF THE INVENTION

The present inventive improved CSF drainage system includes an overfill prevention mechanism that automatically activates when a preset amount of fluid enters the collection chamber, increasing the safety of the patient as well as reducing the workload on hospital staff that otherwise would have to manually and frequently monitor the level.

An aspect of the present invention is directed to an implantable bodily fluid drainage system including a collection vessel and a mechanical volume limiting mechanism for preventing overfill of the collection chamber. In contrast to convention mechanisms, the present inventive mechanical volume limiting mechanism is not susceptible to malfunction if immersed in the bodily fluid.

Another aspect of the present inventive drainage system relates to the collection vessel having an outer collection chamber and an inner collection chamber, wherein the inner collection chamber is axially displaceable within the outer collection chamber. The mechanical volume limiting mechanism includes a bent moveable arm rotatably disposed in the inner collection chamber and supported substantially at its center by a hinge to the fixed supporting arm. A stopper head is disposed at one terminating end of the bent moveable arm and a pinion gear disposed at an opposite terminating end of the bent moveable arm. A rack gear mounted to the inner surface of the inner collection chamber engages the pinion gear rotating the bent moveable arm about the hinge. As the bodily fluid accumulates in the inner collection chamber, the inner collection chamber travels axially downward relative to the outer collection chamber while the pinion gear on the bent moveable arm engages with the rack gear thereby raising the stopper head upwards, eventually closing off the inlet port of the outer collection chamber.

Still another aspect of the present invention relates to an implantable bodily fluid drainage system with an adjustable volume capacity mechanism for varying a maximum volume capacity of the inner collection chamber. The adjustable volume capacity mechanism includes a coil spring disposed in the outer collection chamber, wherein the coil spring has a spring tension in an absence of an externally applied axial force. The adjustable volume capacity mechanism further includes a spring force adjustment mechanism for generating an externally applied axial force to vary the spring tension of the coil spring. Increasing the spring tension of the coil spring increases the volume capacity of the inner collection chamber; whereas decreasing the spring tension of the coil spring reduces the volume capacity of the inner collection chamber. In one configuration the spring force adjustment mechanism includes: a threaded shaft inserted through a hole defined in the bottom surface of the outer collection chamber. A first end of the threaded shaft is disposed inside the outer collection chamber, while an opposite second end of the threaded shaft is disposed outside the outer collection chamber. On the first end of the threaded shaft is a supporting plate while a knob is disposed on the second end of the threaded shaft. The coil spring is disposed between the bottom surface of the inner collection chamber and the supporting plate. A knob is disposed on the second end of the threaded shaft.

While yet another aspect of the present invention is direction to an implantable bodily fluid drainage system including a resistance adjustment mechanism disposed at the inlet port of the collection chamber. The resistance adjustment mechanism includes a luer fitting and a selection guide received within a side slot defined in the luer fitting and having a plurality of openings defined therein of varying diameters. The selection guide is slidable within the side slot in a direction perpendicular to an axial direction of the luer fitting so that a desired one of the plural openings of the selection guide is aligned with a lumen defined through the luer fitting. Alternatively, the resistance adjustment mechanism may be configured to include a luer fitting and a collar having defined therein a plurality of openings each differing in diameter. The collar is rotatable so that a desired one of the plural openings is aligned with a lumen defined through the luer fitting.

In yet another aspect of the present invention an implantable bodily fluid drainage system includes a gravity shutoff valve disposed at the inlet port of the collection vessel. The gravity shut off valve includes: (i) a first ball bearing secured within a complementary first hemispherical shape recess by a first compression spring; and (ii) a second ball bearing also secured within a complementary second hemispherical shape recess by a second compression spring. The second ball bearing is separated a predetermined distance from the first ball bearing in a direction of flow of the bodily fluid. The first and second compression springs compress the first and second ball bearings, respectively, in 180° opposing directions along an axis perpendicular to a direction of flow of fluid through the gravity shut off valve. The first and second hemispherical shape recesses each transitioning in the direction of flow of the bodily fluid into respective linear pathways sloping downward at approximately 45° relative to the axis perpendicular to the direction of flow of fluid through the gravity shut off valve. In the direction of flow of fluid through the gravity shut off valve, after each of the first and second hemispherical shape recesses, an axial passageway of the valve narrows to prevent the respective first and second ball bearings from passing therethrough.

While yet another aspect of the present invention relates to an implantable bodily fluid drainage system in which the collection vessel includes a primary collection chamber and the mechanical volume limiting mechanism includes a moveable arm formed from three branches each having a terminating end and an opposite end sharing a common intersection point. A first terminating end of a first branch of the moveable arm is rotatably mounted to an inner surface of the primary collection chamber via a hinge. A stopper head and flotation member respectively are disposed at terminating ends of the remaining two branches of the moveable arm. The floatation member rises simultaneously with the fluid level in the primary collection chamber. Eventually, the stopper head seats in an inlet port of the primary collection chamber closing it off and preventing overfilling of the primary collection chamber. The moveable arm may be T-shaped or Y-shaped.

In another aspect of the present invention an implantable bodily fluid drainage system with a mechanical volume limiting mechanism includes a central flotation member disposed inside a collection vessel having an inlet port defined in a top surface of the collection vessel. The central floatation member has an opening defined axially therethrough. A stopper head mounted on an upper surface of the central floatation member is aligned in an axial direction with the inlet port of the collection vessel. An axle mounted to a bottom surface of the collection vessel extends axially upwards towards the top surface of the collection chamber with the axle passing through the opening defined in the central floatation member. A radial cross-section of the opening in the central floatation member and a radial cross-section of the axle may be complementary and non-circular.

Another aspect of the invention is directed to an implantable bodily fluid drainage system in which the collection vessel is configured as a two-part telescopic design comprising an upper housing tubular section and a lower housing tubular section. Each of the upper and lower housing tubular sections having an open end and an opposite closed end. The open end of the lower housing tubular section is nested within the open end of the upper housing section. Complementary teeth are arranged on mating surfaces of the upper and lower housing sections, respectively, that are in physical contact with one another. Disposed between the mating surface of the upper and lower housing sections is an O-ring. The volume capacity of the collection vessel is adjustable by axially displacing the lower housing tubular section relative to the upper housing tubular section.

In still yet another aspect of the invention is directed to an implantable bodily fluid drainage system with a volume limiting mechanism including a flexible tubing having a secured end and an opposite free terminating end. The secured end of the flexible tubing is inserted into an inlet port defined in a top surface of the collection vessel, while the free terminating end of the flexible tubing extends into the collection vessel. Fluid passes through a lumen defined axially through the flexible tubing. A flotation member is disposed about the free terminating end of the flexible tubing, wherein the floatation member rises axially simultaneously with fluid level of bodily fluid accumulated in the collection vessel. At some point with the rise of the floatation member, the flexible tubing bends forming a kink that tapers the flow of bodily fluid therethrough. Eventually, the bend in the flexible tubing forms an angle ≤90° cutting off all flow of fluid therethrough.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which:

FIG. 5A is a partial cross-sectional view of a third embodiment with a Y-shaped hinged floatation member overfill prevention mechanism and multi-stage auxiliary collection chambers for increased volume capacity functionality comprising part of a bodily fluid drainage system in accordance with the present invention, wherein the inlet port is closed off by the stopper head after filling the primary chamber;

FIG. 5B is a partial cross-sectional view of the third embodiment of FIG. 5A in which, after the primary chamber has been filled to capacity, the respective valves of the auxiliary chambers are opened to increase volume capacity and the inlet port is reopened to allow additional bodily fluid to be collected;

DETAILED DESCRIPTION OF THE INVENTION

The present inventive volume limiting mechanisms and volume capacity adjustment mechanisms are used as part of an implantable drainage system for draining a bodily fluid, such as CSF.

Figure 1A:
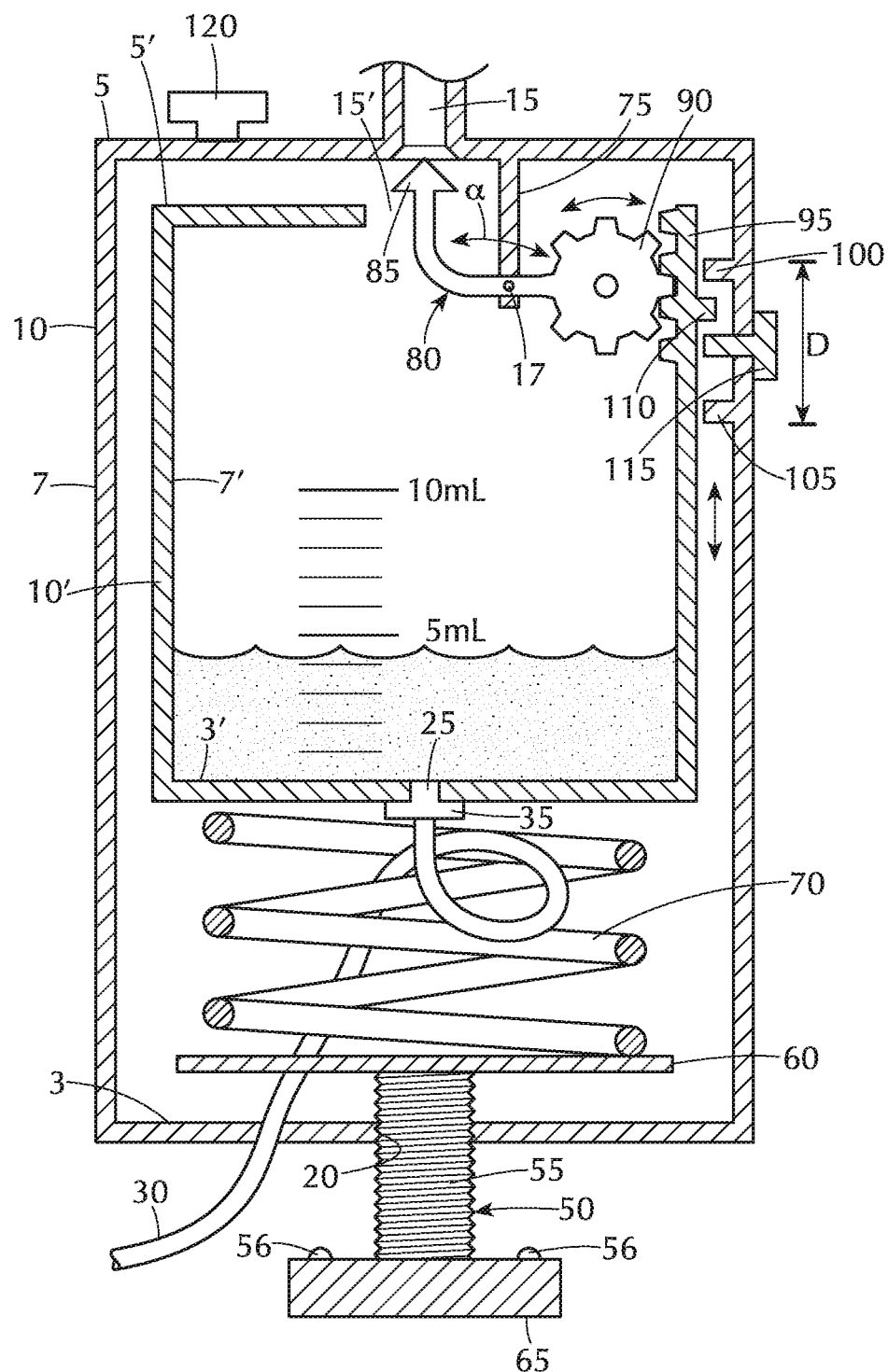
FIG. 1A is a partial cross-sectional view of a first embodiment with a rack-and-pinion overfill prevention mechanism and a coil spring operated adjustable volume capacity functionality comprising part of a bodily fluid drainage system in accordance with the present invention, wherein the drainage system is in an open state.

FIG. 1A is a partial cross-sectional view of a first embodiment comprising a rack-and-pinion volume limiting mechanism and a coil spring adjustable volume capacity mechanism for use in an implantable bodily fluid drainage system. The implantable bodily fluid drainage system comprises a pair of collection chambers (one nested within the other) including an outer collection chamber 10 having a top surface 5, an opposite bottom surface 3 and sidewall 7 extending therebetween to form a closed outer container. Disposed within the outer collection chamber 10 is an inner collection chamber 10' having a corresponding top surface 5' an opposite bottom surface 3' and sidewall 7' extending therebetween forming a closed inner container. Inner collection chamber 10' is smaller in dimension relative to that of the outer collection chamber 10. The collection chambers 10, 10' are preferably made of a transparent material and the inner collection chamber 10' has a series of identifying volume capacity markings or lines, preferably in predetermined discrete increments (e.g., 1 ml increment hash marks) with numerical values associated with some, if not all, markings (e.g., numerical indications provided every 5 ml). Top surface 5 of outer collection chamber 10 has an associated inlet port or opening 15 defined therethrough while the top surface 5' of the inner collection chamber 10' has an associated inlet port or opening 15' defined therethrough. The two inlet ports 15, 15' in the respective outer and inner collection chambers 10, 10' are substantially aligned (but not necessarily of equal diameter) so that bodily fluid draining from an implanted catheter at a target site in the body passes through the respective inlet ports 15, 15' and is ultimately collected in the inner collection chamber 10'. No fluid is intended to accumulate in the outer collection chamber 10 outside of the inner collection chamber 10'. Thus, under proper operation all the bodily fluid from the implanted catheter is collected only in the inner collection chamber 10'.

Mounted to an interior surface of one of the walls 7 of the outer collection chamber 10 is a minimum travel limiting stop 100 and a maximum travel limiting stop 105 separated a predetermined distance (D) from one another in a longitudinal direction of the chamber 10. Each travel limiting stop 100, 105 is formed as a rib, nub or other shape projection extending radially inward into the interior of the outer collection chamber 10, preferably substantially perpendicular to sidewall 7. Along an exterior surface of the sidewall 7' of the inner collection chamber 10' is mounted a single axial movement guide 110, such as a rib, nub or other shape projection extending radially outward, preferably substantially perpendicular to sidewall 7', away from the inner collection chamber 10' towards the interior surface of the sidewall 7 of the outer collection chamber 10. Axial movement guide 110 is positioned or trapped, in an axial direction, between the minimum and maximum travel limiting stops 100, 105. Accordingly, axial displacement of the axial movement guide 110 restricts or delimits axial movement or travel of the inner collection chamber 10' relative to the outer collection chamber 10 between the minimum and maximum travel limiting stops 100, 105. The axial movement guide 110 is designed to engage with the minimum and maximum travel limiting stops 100, 105 thus restricting axial movement or travel of the inner collection chamber 10' relative to the outer collection chamber 10 to open/close the inlet port or opening 15. Arranged transversely through the wall 7 of the outer collection chamber 10 between the maximum and minimum travel limiting stops 100, 105 is a bypass switch or valve 115 that is maintained in a locked open state or position as a safety feature in case of overfill of the inner collection chamber 10'.

Figure 1B:
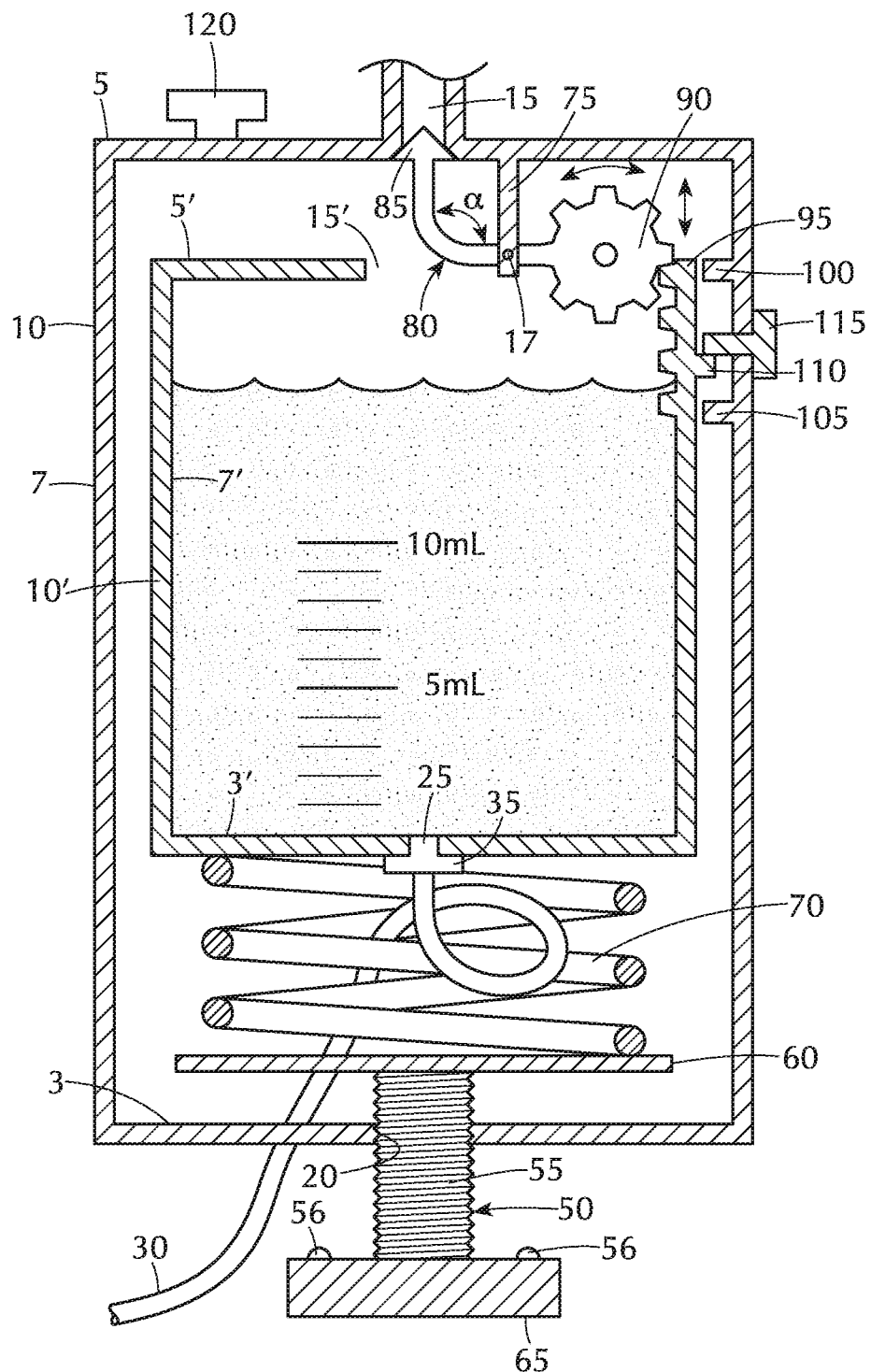
FIG. 1B is a partial cross-sectional view of the first embodiment of FIG. 1A, while in a closed state.

The inlet opening or port 15 of the outer collection chamber 10 is opened/closed to permit/prohibit fluid from flowing therethrough and into the inner collection chamber 10' by a rack-and-pinion mechanically operated stopper head. A fixed supporting arm 75 mounted at one end to the interior surface of the top surface 5 of the outer collection chamber 10 extends substantially perpendicularly into the interior of the outer collection chamber 10 through the inlet port or opening 15' and into the inner collection chamber 10'. A hinge 17 disposed at the opposite end of the fixed supporting arm 75 supports substantially centrally a moveable arm 80 allowing the moveable arm 80 to freely swing or rotate about the hinge 17. Moveable arm 80 has a bent or curved configuration at an angle α, preferably where 90°<α. Pinion gear 90 is disposed at one terminating end of moveable arm 80, while a stopper head 85 is configured at the opposite terminating end of the moveable arm 80. Stopper head 85 is complementary in both size and shape to that of the inlet port 15 so that when the stopper head is seated in the inlet port passage of fluid therethrough is prohibited. Pinion gear 90 matingly engages with a complementary linear rack gear 95 disposed on an interior surface of the sidewall 7' of the inner collection chamber 10'. In FIG. 1A the inlet port or opening 15 of the outer collection chamber 10 is in an open state allowing the bodily fluid to pass therethrough. As fluid accumulates in the inner collection chamber 10' the inner collection chamber 10' moves axially downward relative to the outer collection chamber 10. With the axial displacement of the chambers 10, 10' relative to one another the pinion gear 90 travels along the linear rack gear 95 which, in turn, causes the moveable arm 80 to swing or rotate about the hinge 17 raising the stopper head 85 towards the inlet port or opening 15 of the outer collection chamber 10. FIG. 1B shows the rack-and-pinion volume limiting mechanism of FIG. 1A wherein the stopper head 85 is seated in the inlet port or opening 15 of the outer collection chamber 10 thereby closing it off to the passage of fluid therethrough.

Figure 8:
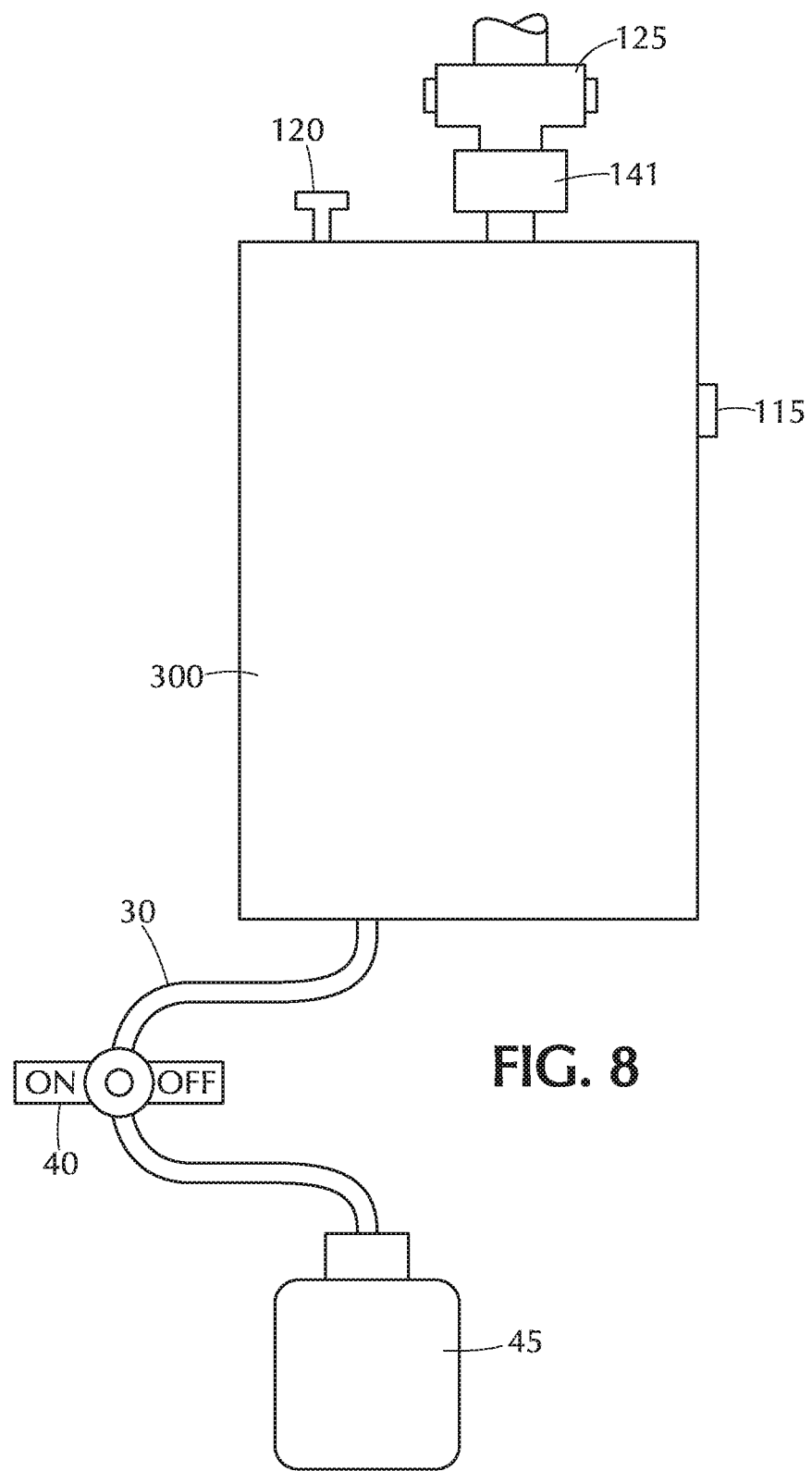
FIG. 8 is a partial side view of the improved drainage system in accordance with the present invention.

Opposite the top surface 5' of the inner collection chamber 10' is a bottom surface 3' having an outlet port or opening 25 defined therein. Tubing 30 insertable into the outlet port or opening 25 and securable in place therein via a fitter, plug or adapter 35, delivers the fluid collected in the inner collection chamber 10' to an external drainage bag 45 or other external collection vessel (FIG. 8). An externally manually operated on/off stopcock or valve 40 disposed along the tubing 30 may be used to regulate the flow of fluid through the tubing 30.

Referring to FIG. 1A, the volume capacity of fluid able to be collected in the inner collection chamber 10' is mechanically adjustable or controllable (increase/decreased), as desired, in accordance with the present invention via a coil spring 70 compressed axially by a mechanical spring force adjustment mechanism 50. The exemplary spring force adjustment mechanism 50 illustrated in this first embodiment of FIG. 1A comprises a threaded shaft 55 having a planar supporting plate 60 at one terminating end of the threaded shaft 55 and knob or dial 65 (preferably, larger in diameter relative to the threaded shaft 55) disposed at an opposite terminating end of the threaded shaft 55. Coil spring 70 is disposed between the bottom surface 3' of the inner collection chamber 10' and the supporting plate 60.

Threaded shaft 55 passes through a slightly larger diameter hole 20 defined through the bottom surface 3 of the outer collection chamber 10 such that the supporting plate 60 is disposed within the outer collection chamber 10 while the knob or dial 65 is disposed outside of the outer collection chamber 10. Both the knob 65 and supporting plate 60 are preferably larger in diameter than the hole 20 to prohibit passage through the hole 20. One or more tactile indicators 56, e.g., bumps, projections, ribs or recesses, are preferably disposed on an under surface of the knob or dial 65 that is substantially parallel to or facing the bottom surface 3 of the outer collection chamber 10. Rotation of the knob or dial 65 increases/decreases depending on the direction of rotation (e.g., clockwise or counter-clockwise) the volume capacity in the internal collection chamber 10'. By way of illustrative example only, each revolution (360° rotation) of the knob or dial 65 clockwise/counter-clockwise, in turn, increases/decreases, respectively, the maximum volume level of fluid in the internal collection chamber 10' by a predetermined amount (e.g., approximately 50 ml) with more granular or smaller predetermined incremental adjustments (e.g., approximately 5 ml increments) provided by each tactile indicator 56.

In operation, increasing the spring tension (i.e., compression) of the coil spring 70 increases the volume capacity of bodily fluid to be accumulated in the inner collection chamber 10' before the force imposed by the accumulated fluid exceeds the counteracting opposing force exerted by the compressed coil spring 70. It is only then that the inner collection chamber 10' travels or moves axially downward toward the bottom 3 of the outer collection chamber 10. Specifically, rotation of the knob or dial 65 in a clockwise direction raises the supporting plate 60 axially upward in the outer collection chamber 10 towards the top surface 5. As the supporting plate 60 travels upward in an axial direction the strength of the external force applied to the coil spring 70 increases causing the spring tension of the coil spring 70 to increase (i.e., more compressed). In this compressed state, a greater volume of fluid may be accumulated in the inner collection chamber 10' before the force exerted by the accumulated volume of fluid exceeds, and thus counteracts, the opposing force exerted by the compressed coil spring 70 allowing the inner chamber 10' to travel axially downward relative to the outer collection chamber 10. As the volume of fluid accumulated in the inner collection chamber 10' increases further the inner collection chamber 10' lowers axially relative to the outer collection chamber 10 causing the pinion gear 90 to travel downward along the rack gear 95 while the stopper head 85 at the opposite end of the moveable arm 80 swings or rotates about hinge 17 upwards. Eventually, the inner collection chamber 10' is displaced in a longitudinal direction (lowered) sufficiently so that the stopper head 85 is seated within and closes off the inlet port or opening 15 thereby preventing overfilling.

Whereas, when the knob or dial 65 is rotated in a counter-clockwise direction the supporting plate 60 travels in a longitudinal direction downward towards the bottom surface 3 thereby reducing the external force applied to the coil spring 70 (i.e., coil spring 70 is more relaxed, less compressed, reduced spring tension). With the coil spring 70 in this more relaxed (i.e., less compressed) state, a smaller volume capacity of fluid may be accumulated in the inner collection chamber 10' before the force exerted by the accumulated fluid exceeds, and thus counteracts, the reduced opposing external force exerted by the coil spring 70 allowing the inner chamber 10' to travel axially downward relative to the outer collection chamber 10. As the volume of fluid accumulated in the inner collection chamber 10' increases still further the inner collection chamber 10' is displaced in a longitudinal direction (lowered) relative to the outer collection chamber 10 whereby the pinion gear 90 travels downward along the rack gear 95 causing the stopper head 85 at the opposite end of the moveable arm 80 to swing or rotate about hinge 17 upwards. Eventually, the inner collection chamber 10' is lowered sufficiently so that the stopper head 85 is seated within and closes off the inlet port or opening 15 preventing overfilling of the chamber.

Thus, compression of the coil spring 70 via the spring force adjustment mechanism 50 increases the amount of fluid able to be accumulated in the inner collection chamber 10' before the inner collection chamber 10' begins to move downward in a longitudinal direction thereby engaging the rack-and-pinion gear volume limiting mechanism. Alternative configurations of the spring adjustment mechanism 50 to control spring tension (i.e., the extent of compression/relaxation) of the coil spring 70 are contemplated and within the intended scope of the present invention.

Figure 4A:
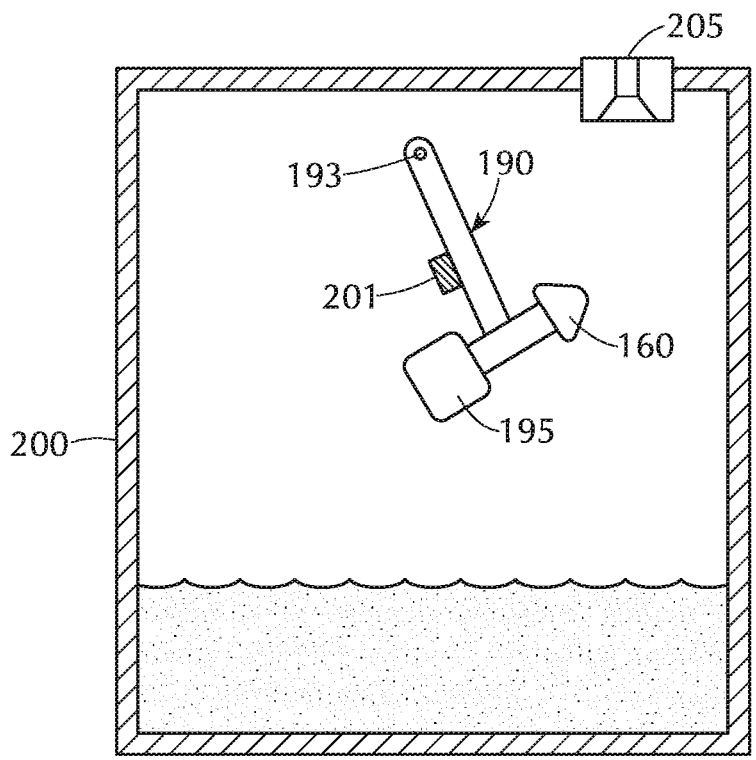
FIG. 4A is a partial cross-sectional view of a second embodiment with a T-shape hinged floatation member overfill prevention mechanism in a single primary collection chamber, wherein the inlet port is in an open state.
Figure 4B:
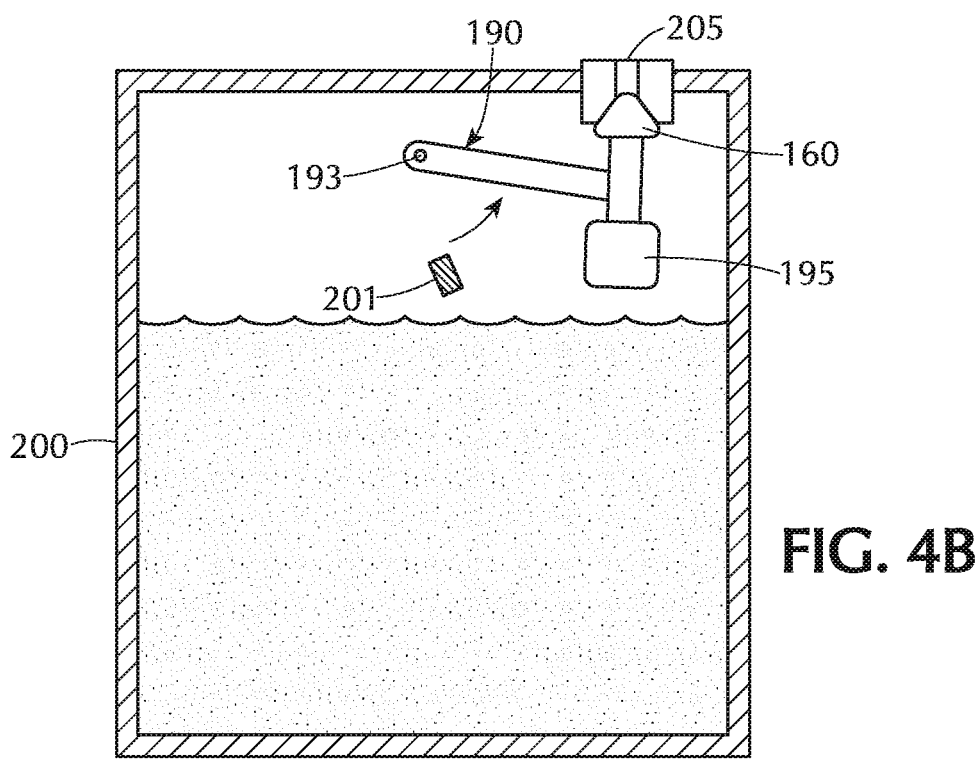
FIG. 4B is a partial cross-sectional view of the second embodiment of FIG. 4A, wherein the inlet port is in a closed state.

FIGS. 4A & 4B illustrate a second embodiment of the volume limiting mechanism in accordance with the present invention. Instead of the coil spring pinion design in accordance with the embodiment in FIGS. 1A & 1B, the alternative confirmation in FIGS. 4A & 4B employs a hinged or rotating floatation member. In this embodiment, a T-shaped arm 190 is rotatably mounted to the collection chamber 200 about a hinge 193. A stopper head 160 and a floatation member 195, respectively, are disposed at opposite ends of the top of the T-shaped arm 190. Stopper head 160 is complementary in size and shape to the inlet port or opening 205. This second embodiment shown in FIGS. 4A & 4B differs from embodiments previously shown and described in that instead of nested inner and outer collection chambers, only a single primary collection chamber 200 is provided. Initially, when the primary collection chamber 200 is free of any fluid the T-shaped arm 190 is swung or rotated about hinge 193 downward so that the inlet port or opening 205 is open to receive the fluid therethrough, FIG. 4A. Prior to the fluid level reaching the floatation member 195, the T-shaped arm 190 preferably rests on a stopping member 201 mounted to an interior surface of the collection chamber 200. Stopping member 201 insures upward movement of the T-shaped arm in a direction towards the inlet port or opening 205 with a rise in fluid level. The floatation member 195 rises upward simultaneously with the fluid level in the primary collection chamber 200, until eventually, the stopper head 160 is seated inside the inlet port or opening 205 closing it off and preventing overfilling of the primary collection chamber 200 (FIG. 4B).

A third hinged-floatation volume limiting mechanism of the present invention is illustrated in FIGS. 5A & 5B. In this embodiment, a Y-shaped arm 190' with formed from three branches having a common intersection point. A first terminating end (opposite the common intersection point) of a first branch of the arm 190' is rotatably mounted to a fixed supporting arm 75' via a hinge 193. The fixed supporting arm 75' is mounted to an inner surface of a top surface of a collection chamber. At the terminating ends (opposite the common intersection point) of the remaining two branches of the Y-shaped arm 190' is disposed a stopper head 160 and a floatation member 195, respectively. Stopper head 160 is complementary in size and shape to the inlet port or opening 205. This third embodiment shown in FIGS. 5A & 5B differs from embodiments previously shown and described in that instead of nested inner and outer collection chambers, only a single primary collection chamber 200 is provided. Initially, when the primary collection chamber 200 is free of any fluid the Y-shaped arm 190' is swung or rotated about hinge 193 downward so that the inlet port or opening 205 is open to receive the fluid therethrough. The flotation member 195 rises upward simultaneously with the fluid level in the primary collection chamber 200, until eventually, the stopper head 160 is seated inside the inlet port or opening 205 closing it off and preventing overfilling of the primary collection chamber 200 (FIG. 5A). One or more auxiliary collection chambers 210, 210' may be provided in fluid communication with the single primary collection chamber 200 to increase the volume capacity, i.e., increase the maximum amount of fluid able to be collected. Each auxiliary collection chamber 210, 210' has an associated shut off valve 215, 215'. By manually opening the shut off valve 215, 215' additional fluid is permitted to flow from the primary collection chamber 200 into the first auxiliary collection chamber 210 thereby increasing the overall maximum volume capacity of fluid able to be collected. If still additional storage capacity is required, the shut off valve 215' of the secondary auxiliary collection chamber 210' may be opened allowing the fluid to flow from the first auxiliary collection chamber 210 into the second auxiliary collection chamber 210', as depicted in FIG. 5B. Only two auxiliary collection chambers 210, 210' are illustrated in FIGS. 5A & 5B, however any number of one or more auxiliary collection chambers may be employed, as desired.

Figure 6A:
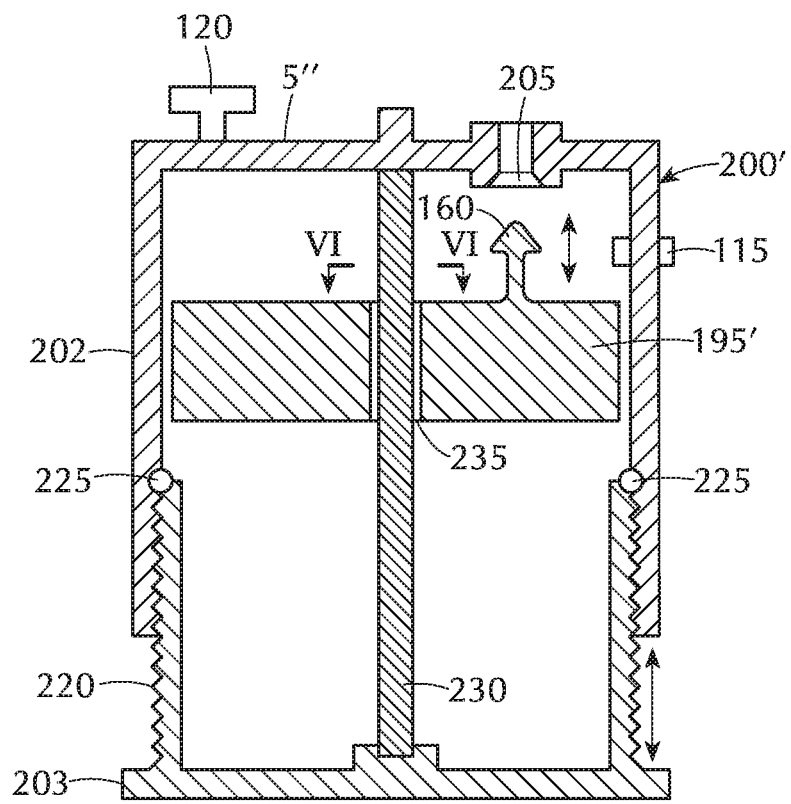
FIG. 6A is a partial cross-sectional view of a fourth embodiment with a center floatation member overfill prevention mechanism and a two-part telescopic collection chamber configuration to provide adjustable volume capacity functionality comprising part of a bodily fluid drainage system in accordance with the present invention, wherein the drainage system is in an open state.
Figure 6B:
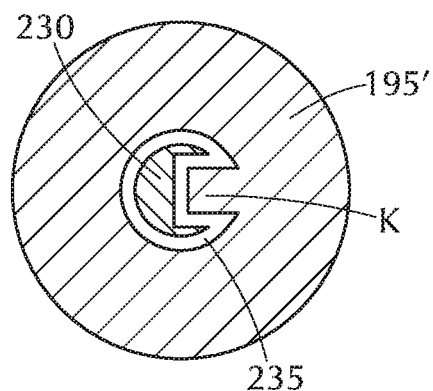
FIG. 6B is a cross-sectional view along lines VI-VI in FIG. 6A.

FIG. 6A is yet another embodiment of a centered floatation member 195' volume limiting mechanism for preventing overfilling. This embodiment like that in FIGS. 5A & 5B also has a single collection chamber 200', but in this embodiment the single collection chamber 200' is configured as a two-part telescopic design comprising an upper housing tubular section 202 and a lower housing tubular section 203, each of the upper and lower housing tubular sections 202, 203 having an open end and an opposite closed end. The open end of the lower housing tubular section 203 is nested within the open end of the upper housing section 202. Complementary teeth 220 are arranged on mating surfaces of the upper and lower housing sections 202, 203, respectively, that physical engage with one another. An O-ring or other type of seal 225 is disposed between the mating surface of the upper and lower housing sections 202, 203. Accordingly, the maximum volume capacity of the single collection chamber 200' may be increased/decreased by sliding the lower housing tubular section 203 downward/upward relative to the upper housing tubular section 202. A single centered flotation member 195', preferably in the shape of a disk is disposed within the single collection chamber 200'. Projecting, preferably substantially perpendicularly, from an upper surface of the floatation member 195' towards the top surface 5" of the single collection chamber 200' is a stopper head 160 aligned vertically/axially with the inlet port or opening 205. The stopper head 160 is complementary in size and shape to the inlet port or opening 205. A center axle or shaft 230 passes through a center opening 235 defined in the floatation member 195'. The center axle 230, preferably has a non-circular cross-section in a direction perpendicular to the axial direction, while the center opening 235 defined in the floatation member 195' has a complementary shape. In the exemplary embodiment of FIG. 6B, the center axle 230 has a keyed cross-section (e.g., notch "K"), while the center opening 235 defined in the flotation member 195' has a complementary keyed cross-section. This keyed non-circular cross-sectional configuration of both axle 230 and corresponding opening 235 prevents rotation of the floatation member 195' about the axle 230 thereby insuring that the stopper head 160 is properly aligned with the inlet port or opening 205 of the single collection chamber 200' at all times. Flotation member 195' rises simultaneously with fluid level in the single collection chamber 200'. Eventually, the stopper head 160 is seated within in and closes off the inlet port or opening 205 thereby preventing the passage of fluid into and overfill of the single collection chamber 200'.

Figure 7A:
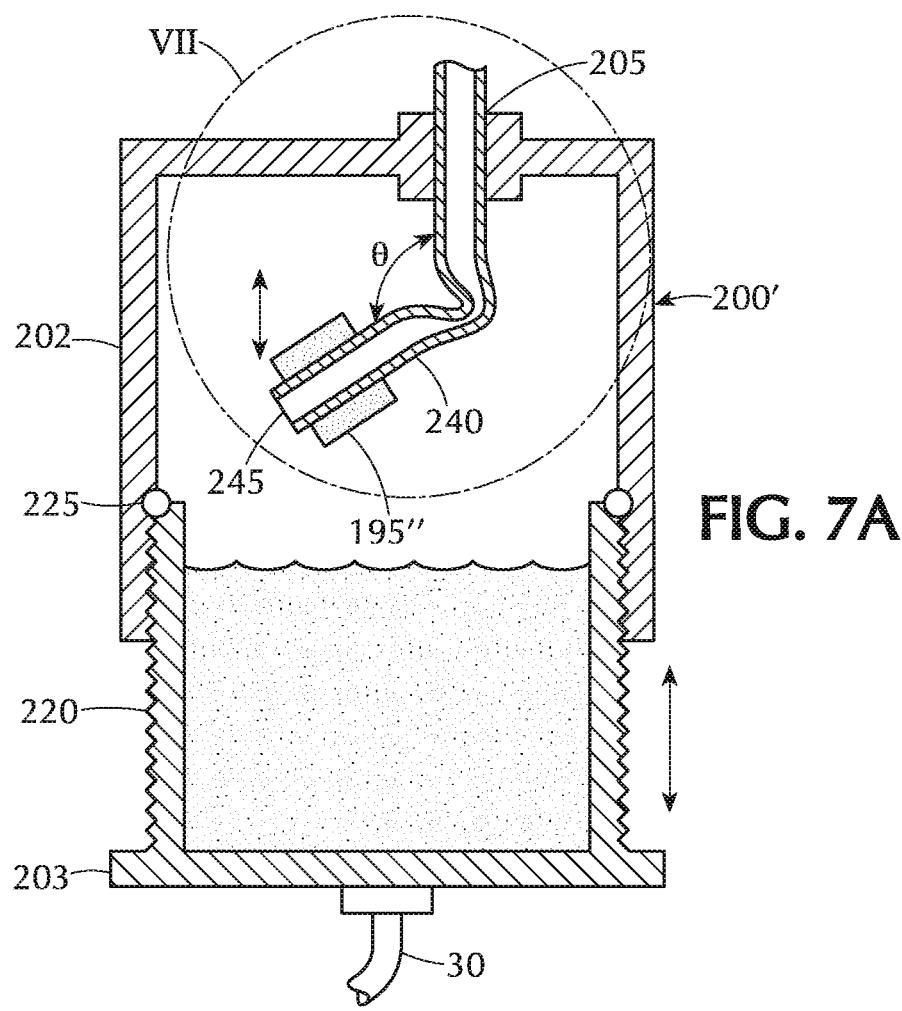
FIG. 7A is a partial cross-sectional view of a fifth embodiment with a kinked tubing volume limiting mechanism and a two-part telescopic collection chamber configuration to provide adjustable volume capacity functionality comprising part of a bodily fluid drainage system in accordance with the present invention, wherein the drainage system is in an open state.
Figure 7B:
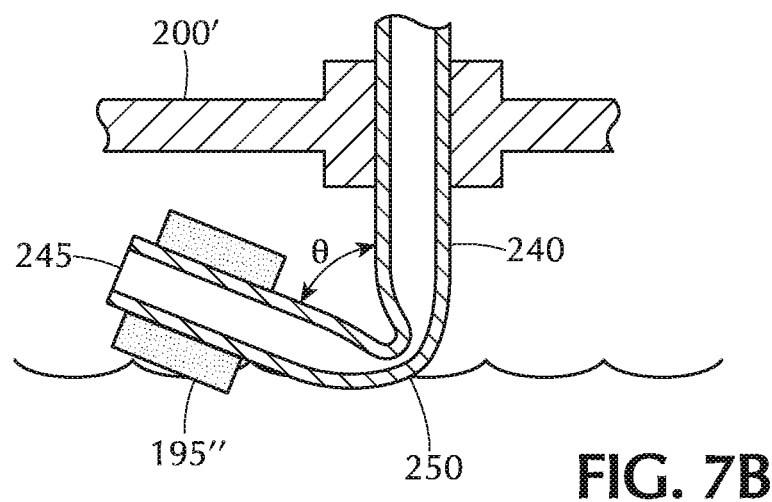
FIG. 7B is an enlarged view of a section of the kinked tubing as denoted by the dashed circle VII in FIG. 7A, wherein the drainage system is in a closed state.

The last embodiment of the present invention is a kinked tube mechanism design for the volume limiting functionality, as illustrated in FIGS. 7A & 7B. Similar to that shown and described in the embodiment in FIG. 6A, the embodiment in FIGS. 7A & 7B also has a single collection chamber 200' having a two-part telescopic design comprising an upper housing tubular section 202 and a lower housing tubular section 203, each of the upper and lower housing tubular sections 202, 203 having an open end and an opposite closed end. The open end of the lower housing tubular section 203 is nested within the open end of the upper housing section 202. Complementary teeth 220 are arranged on mating surfaces of the upper and lower housing sections 202, 203, respectively, that physical engage with one another. An O-ring or other type of seal 225 is disposed between the mating surface of the upper and lower housing sections 202, 203. Accordingly, the maximum permissible volume capacity of the single collection chamber 200' may be increased/decreased by sliding the lower housing tubular section 203 downward/upward relative to the upper housing tubular section 202.

A flexible tubing 240 is secured at one end in the inlet port or opening 205 while its opposite free terminating end 245 extends into the single collection chamber 200' without being connected or secured to anything. The free terminating end 245 of the flexible tubing 240 is open. Mounted or secured to the free terminating end 245 of the flexible tubing 240 is a floatation member 195" such as a cylindrical washer. The floatation member 195" rises simultaneously with the fluid level in the single collection chamber 200'. Eventually, the fluid level in the single collection chamber 200' rises to the point that the flexible tubing 240 bends forming a kink 250 that reduces the flow of fluid through the inlet port or opening 205 to a tapered titration and with sufficient rise of the flotation member 195" eventually cuts off all flow completely (when the kink in the flexible tubing 240 forms an acute angle θ≤90°. In contrast to the embodiments discussed heretofore in which the volume limiting mechanism (i.e., overfill prevention mechanism) itself does not provide any restriction of fluid flow (i.e., the inlet port or opening is either open or closed), this flexible tubing overfill prevention mechanism produces a restricted, tapered or weening of the fluid flow as the flexible tubing 240 bends until a complete cessation reduced flow (when the flexible tubing 240 is bent at an angle θ≤90° (FIG. 7B). The material selected and the length of the flexible tubing 240 is sufficiently long so that in response to the flotation member 195" being raised or lifted the flexible tubing 240 is able to bend at angle θ≤90° without having to apply any additional external force. Preferably, flexible tubing 240 is made from a biocompatible material and has a length appropriate to the size of the collection chamber to allow its operation. It is also contemplated that the flexible tubing 240 be intentionally designed during manufacture to include a minor bend or kink prior to assembly in the drainage system to insure that the flexible tubing 240 bends at the desired location when the flotation member 195" rises with the fluid level in the single collection chamber 200'.

FIG. 8 is a partial side view of the improved drainage system in accordance with the present invention wherein, for simplicity of illustration only, the one or more collection chambers for each embodiment, as described in detail in the preceding paragraphs, has been generically represented by a single rectangular collection vessel 300. The specific configuration of the one or more collection chambers for each of the embodiments may be substituted for the generically represented rectangular collection vessel 300. For any of the foregoing described embodiments, the collection chamber preferably incorporates several backup safety features such as a hydrophobic filter 120 and/or bypass valve 115. The hydrophobic filter 120 in the top surface 5 of the outer collection chamber 5 reduces the risk of contamination of the sterile internal portions of the components of the present inventive drain system should they undesirably come into contact with the fluid being drained in the event of overfilling of the collection chamber. A bypass switch or valve 115 may be provided in the collection chamber of any of the embodiments of the drainage system described herein. The bypass switch is maintained in a locked open state or position as an additional safety feature in case of overfill of the collection chamber in which the fluid is stored.

Figure 2A:
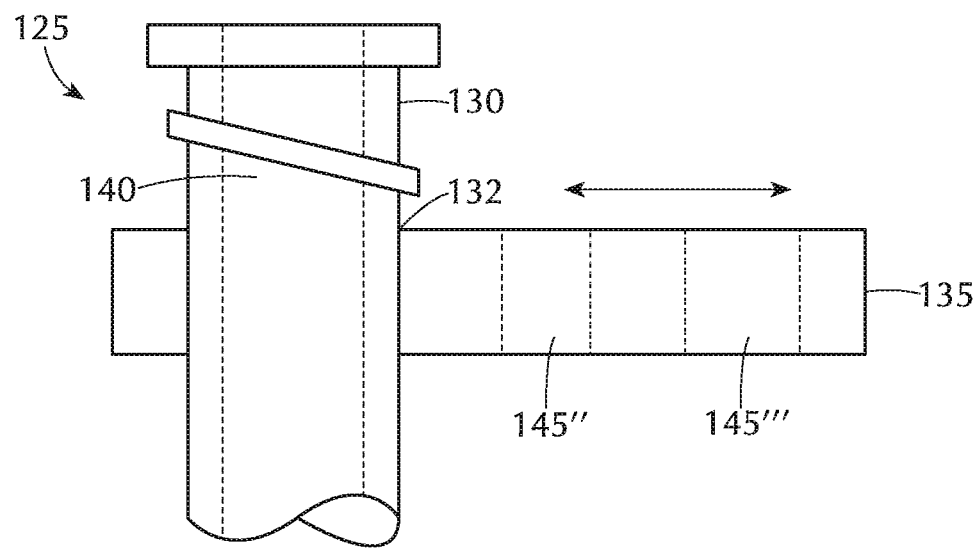
FIG. 2A is a side view of one exemplary configuration of the luer lock of FIG. 8.
Figure 2B:
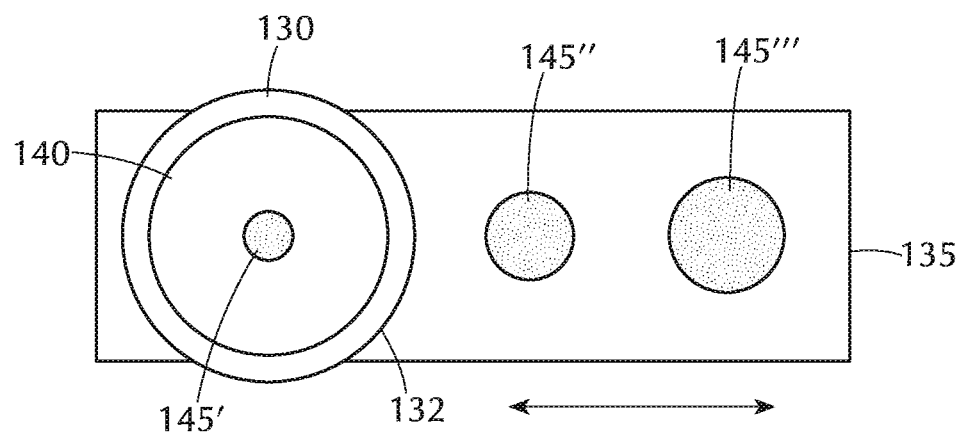
FIG. 2B is a top view of the luer lock of FIG. 2A.
Figure 2C:
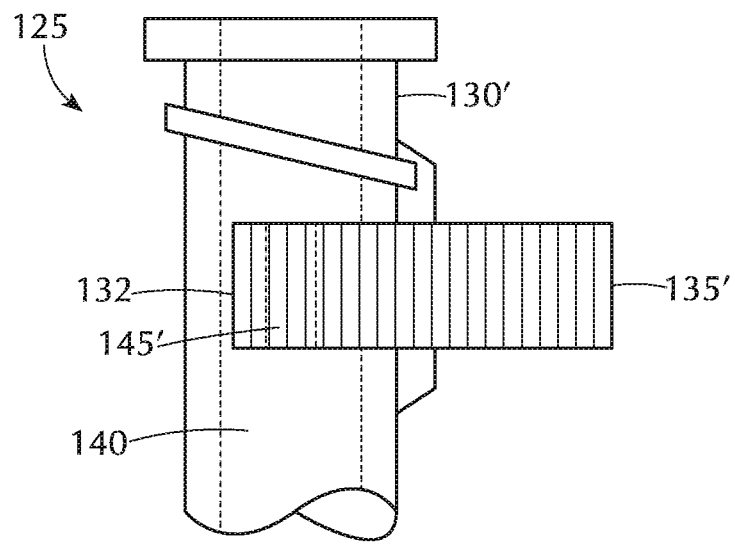
FIG. 2C is a side view of another exemplary configuration of the luer lock of FIG. 8.
Figure 2D:
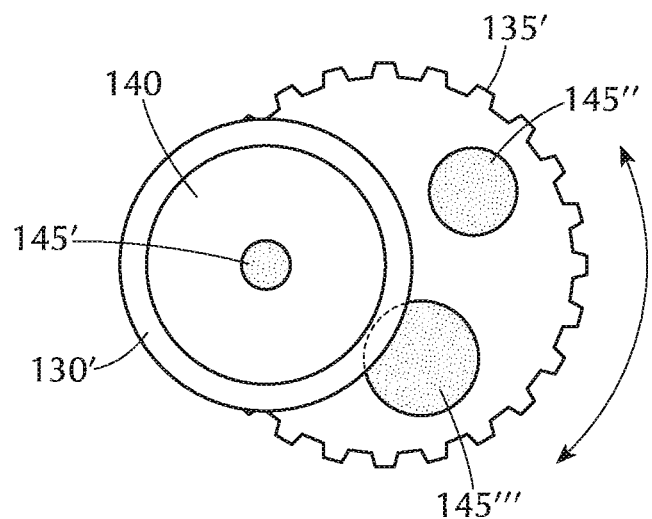
FIG. 2D is a top view of the luer lock of FIG. 2C.

Not only may the volume capacity of the inner collection chamber 10' be adjusted or controlled in accordance with the present invention, the flow rate of the bodily fluid entering the collection chamber may also be varied, as desired. The rate of flow of fluid may be controlled or adjusted, in any of the aforementioned embodiments in accordance with the present invention, using a resistance adjustment mechanism 125 (FIG. 8). FIGS. 2A & 2B represent side and top views of a first embodiment of the resistance adjustment mechanism 125 in FIG. 8 that comprises a luer fitting 130 and a selection guide 135 received within a side slot 132 of the luer fitting. In the exemplary embodiment illustrated, selection guide 135 has three openings (145', 145", 145'") of varying diameters. One of the openings (145', 145", 145'") is selected by sliding the selection guide 135 in a direction (as indicated by the directional arrows) perpendicular to the axial direction of the luer fitting 130 until the desired diameter opening aligns with the single uniform axial lumen 140 of the luer 130. Any number of one or more different sized diameter openings may be integrated on a single selection guide 135, otherwise a set of separate distinct guides may be utilized, with a different diameter opening associated with each separate guide in the set. An alternative embodiment of the resistance adjustment mechanism 125 is illustrated in FIGS. 2C & 2D including a fitting luer 130' and a rotatable collar 135'. As depicted in the top view in FIG. 2D, collar 135' may be designed to have a plurality of openings (145', 145", 145''') each differing in diameter. In the example illustrated in FIG. 2D three different size diameter openings (145', 145", 145''') are provided. Any number of one or more diameter openings having different diameters may be employed. The desired flow rate of fluid is controlled by rotating the collar 135' so that the desired size diameter opening (145', 145", 145''') aligns with the axial lumen 140 defined in the luer fitting 130'.

Figure 3:
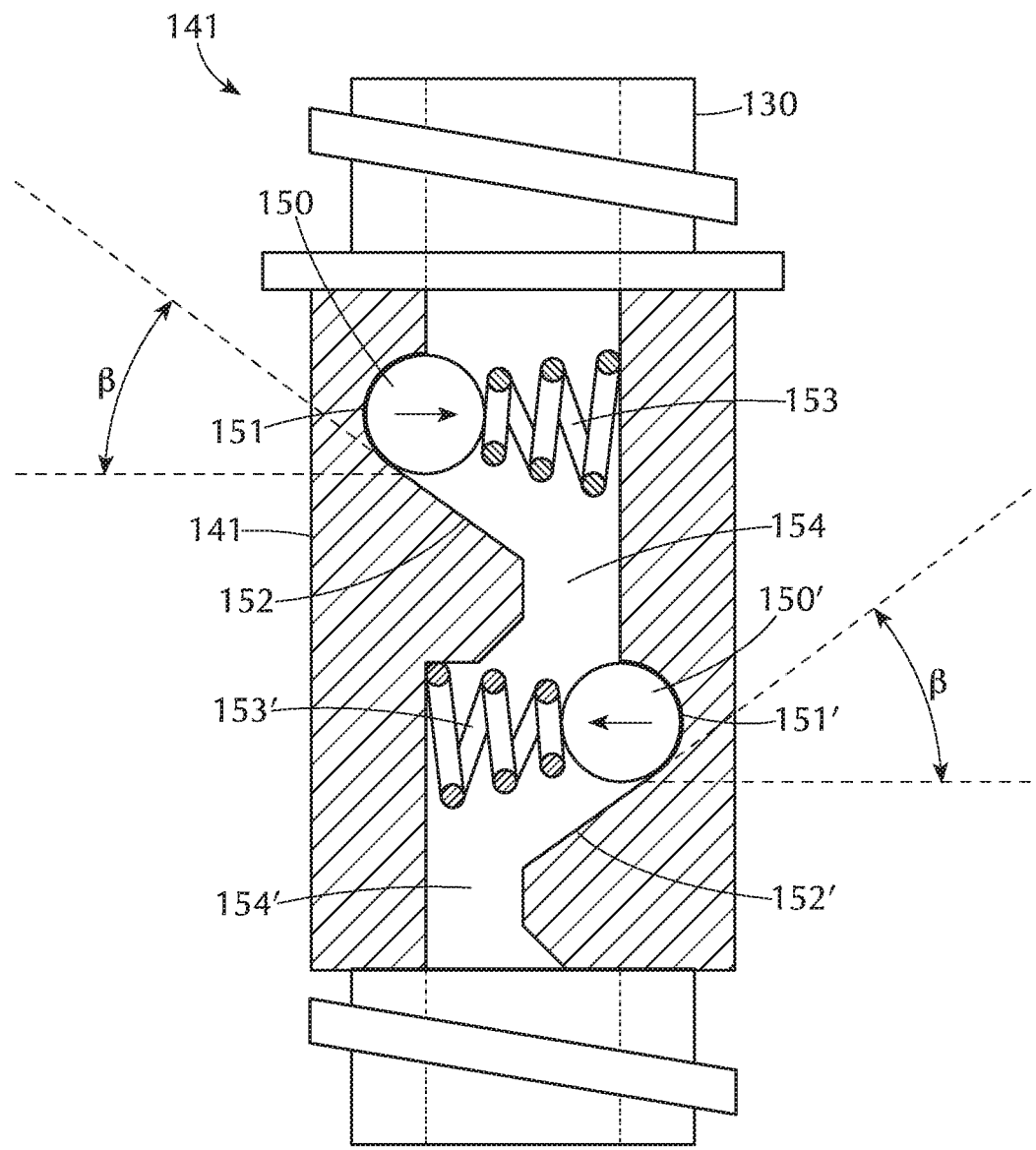
FIG. 3 is a partial cross-sectional view of an exemplary gravity shutoff valve in FIG. 8.

In use, the present inventive implantable drainage system may be subject to possible leakage of fluid from the inner or outer collection chambers 10', 10 with extreme movement by the patient if a supporting pole from which the collection chambers are hung should tip, tilt, lean, slope, list or be knocked over completely. It is estimated that tipping, tilting, leaning, sloping or listing of the supporting pole (with the collection chambers 10, 10' hung therefrom) greater than or equal to a predetermined angle (e.g., approximately 45°) relative to that of a vertical axis perpendicular to the floor on which the supporting pole stands would be at risk to possible leakage of fluid from the inner or outer collection chambers 10', 10. FIG. 3 is an enlarged cross-sectional via of the gravity shutoff valve 141 of FIG. 8. Gravity shutoff valve 141 located at the inlet port or opening 15 of the outer collection chamber 10 provides an additional safety feature to prevent or minimize leakage of the fluid from the inner and outer collection chambers 10', 10 in the event the supporting pole (and, in turn, the collection chambers 10, 10' hung therefrom) tips, tilts, leans, slopes, lists or is even knocked over greater than a desired predetermined angle (e.g., approximately 45°) relative to that of a vertical axis perpendicular to the floor on which the supporting pole stands.

Referring to the enlarged cross-sectional view in FIG. 3, the gravity shutoff valve 141 includes a first ball bearing 150 and a second ball bearing 150' separated a predetermined distance from one another in an axial direction of the luer fitting 130. First ball bearing 150 is secured within a complementary hemispherical shape recess 151 by a first compression spring 153 oriented perpendicular to the axial direction of the luer fitting 130. The hemispherical shape recess 151 transitions downward in a direction of fluid flow through the luer fitting 130 into a linear pathway 152 having a downward slope defined by an angle β, preferably approximately 45°, relative to the horizontal axis (perpendicular to the axial direction of the luer fitting 130). In a similar fashion, the second ball bearing 150' is secured within a complementary hemispherical shape recess 151' by a second compression spring 153'. The hemispherical shape recess 151' transitions downward in the direction of fluid flow into a linear pathway 152' sloping downward at an angle β, preferably approximately 45°, relative to the horizontal axis (perpendicular to the axial direction of the luer fitting 130). In the luer fitting 130, downstream (in a direction of fluid flow) following each of the hemispherical shape recesses 151, 151', the axial passageway 154, 154' narrows to prevent the respective first and second ball bearings 150, 150' from passing therethrough. The first and second compression springs 153, 153' compress the first and second ball bearings 151, 151', respectively, horizontally in 180° opposing directions to address potential tipping, tilting, leaning, sloping or listing of the supporting pole (and collection chambers 10, 10' hung therefrom) in two different opposing directions. Any unwanted or undesired tipping, tilting, leaning, sloping, listing or knocking over of the supporting pole from which the collection chambers 10, 10' are hung beyond the predetermined angle (e.g., approximately 45°) results in the force imposed by one of the ball bearings 151, 151' to counterbalance the force exerted by the respective compression spring 153, 153'. As a result, one of the ball bearings 151, 151' rolls down the associated linear pathway 152, 152' and becomes seated in the associated narrow passageway 154, 154' preventing fluid leakage.

It is advantageous that the mechanical volume limiting mechanisms in accordance with the present invention do not interact with electromagnetic fields and therefore are not susceptible to interference and potential malfunction.

It is also contemplated and within the intended scope of the present invention for the resistance adjustment mechanism 125 and/or gravity shutoff valve 141 to be used with any of the embodiments discussed in any embodiment herein described and illustrated.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A bodily fluid drainage system, comprising:
 a collection vessel having an inlet port receiving drained bodily fluid therethrough into the collection vessel;
 a mechanical volume limiting mechanism for occluding the inlet port preventing overfill of the collection vessel;
 wherein the mechanical volume limiting mechanism is not susceptible to malfunction if immersed in the bodily fluid;
 a gravity shutoff valve disposed at the inlet port of the collection vessel, wherein the gravity shut off valve comprises:
 a first ball bearing secured within a complementary first hemispherical shape recess by a first compression spring;
 a second ball bearing separated a predetermined distance from the first ball bearing in a direction of flow of the bodily fluid, the second ball bearing is secured within a complementary second hemispherical shape recess by a second compression spring; wherein the first and second compression springs compress the first and second ball bearings, respectively, in 180° opposing directions along an axis perpendicular to a direction of flow of fluid through the gravity shut off valve;

the first hemispherical shape recess transitioning in the direction of flow of the bodily fluid into a first linear pathway sloping downward at approximately 45° relative to the axis perpendicular to the direction of flow of fluid through the gravity shut off valve; the second hemispherical shape recess transitioning in the direction of flow of the bodily fluid into a second linear pathway sloping downward at approximately 45° relative to the axis perpendicular to the direction of flow of fluid through the gravity shut off valve;

in the direction of flow of fluid through the gravity shut off valve, after each of the first and second hemispherical shape recesses, an axial passageway of the valve narrows to prevent the respective first and second ball bearings from passing therethrough;

wherein the bodily fluid flows freely through the axial passageway of the valve when: (i) the first ball bearing is secured within the complementary first hemispherical shape recess by the first compression spring; and (ii) the second ball bearing is secured within the complementary second hemispherical shape recess by the second compression spring.

2. The bodily fluid drainage system according to claim 1, wherein the collection vessel comprises:

an outer collection chamber having a top surface, an opposite bottom surface and a sidewall extending therebetween; the top surface of the outer collection chamber having an inlet port defined therethrough;

an inner collection chamber having a top surface, an opposite bottom surface and a sidewall extending therebetween; the inner collection chamber being disposed within the outer collection chamber; the top surface of the inner collection chamber having an inlet port defined therethrough; the inlet port of the inner and outer collection chambers being aligned;

wherein the inner collection chamber is axially displaceable within the outer collection chamber;

wherein the mechanical volume limiting mechanism comprises:

a fixed supporting arm mounted to an inner surface of the outer collection chamber;

a bent moveable arm rotatably disposed in the inner collection chamber and supported substantially at its center by a hinge to the fixed supporting arm; a stopper head disposed at one terminating end of the bent moveable arm and a pinion gear disposed at an opposite terminating end of the bent moveable arm;

a rack gear mounted to the inner surface of the inner collection chamber so as to engage the pinion gear and rotate the bent moveable arm about the hinge;

wherein as the bodily fluid accumulates in the inner collection chamber, the inner collection chamber travels axially downward relative to the outer collection chamber while the pinion gear on the bent moveable arm engages with the rack gear thereby raising the stopper head upwards, eventually closing off the inlet port of the outer collection chamber.

3. The bodily fluid drainage system according to claim 2, further comprising an adjustable volume capacity mechanism for varying a maximum volume capacity of the inner collection chamber; the adjustable volume capacity mechanism comprising:

a coil spring disposed in the outer collection chamber; the coil spring have a spring tension in an absence of an externally applied axial force;

a spring force adjustment mechanism for generating an externally applied axial force to vary the spring tension of the coil spring;

wherein increased spring tension of the coil spring increases the volume capacity of the inner collection chamber; whereas decreased spring tension of the coil spring reduces the volume capacity of the inner collection chamber.

4. The bodily fluid drainage system according to claim 3, wherein the spring force adjustment mechanism comprises:

a threaded shaft inserted through a hole defined in the bottom surface of the outer collection chamber; wherein a first end of the threaded shaft is disposed inside the outer collection chamber, while an opposite second end of the threaded shaft is disposed outside the outer collection chamber;

a supporting plate disposed on the first end of the threaded shaft; wherein the coil spring is disposed between the bottom surface of the inner collection chamber and the supporting plate;

a knob disposed on the second end of the threaded shaft.

5. The bodily fluid drainage system according to claim 2, further comprising:

a maximum travel limiting stop and a minimum travel liming stop, the maximum and minimum travel limiting stops projecting from an interior surface of the wall of the outer collection chamber;

an axial movement guide projecting from an exterior surface of the wall of the inner collection chamber; axial movement of the inner collection chamber within the outer collection chamber is limited by displacement of the axial movement guide between the maximum and minimum travel limiting stops.

6. The bodily fluid drainage system according to claim 1, further comprising a resistance adjustment mechanism disposed at the inlet port of the collection vessel, wherein the resistance adjustment mechanism includes a luer fitting and a selection guide received within a side slot defined in the luer fitting; the selection guide having a plurality of openings defined therein of varying diameters; the selection guide being slidable within the side slot in a direction perpendicular to an axial direction of the luer fitting so that a desired one of the plural openings of the selection guide is aligned with a lumen defined through the luer fitting.

7. The bodily fluid drainage system according to claim 1, further comprising a resistance adjustment mechanism disposed at the inlet port of the collection vessel, wherein the resistance adjustment mechanism includes a luer fitting and a collar; wherein the collar has defined therein a plurality of openings each differing in diameter; the collar is rotatable so that a desired one of the plural openings is aligned with a lumen defined through the luer fitting.

8. The bodily fluid drainage system according to claim 1, wherein the collection vessel includes a primary collection chamber and the mechanical volume limiting mechanism comprises:

a moveable arm formed from three branches each having a terminating end and an opposite end sharing a common intersection point; a first terminating end of a first branch of the moveable arm is rotatably mounted to an inner surface of the primary collection chamber via a hinge; a stopper head and flotation member respectively are disposed at terminating ends of the remaining two branches of the moveable arm;

wherein the floatation member rises simultaneously with the fluid level in the primary collection chamber; eventually, the stopper head seats in an inlet port of the primary collection chamber closing it off and preventing overfilling of the primary collection chamber.

9. The bodily fluid drainage system according to claim 8, wherein the moveable arm is T-shaped or Y-shaped.

10. The bodily fluid drainage system according to claim 8, wherein the collection vessel further comprises at least one auxiliary collection chamber in fluid communication with the primary collection chamber to adjust the volume capacity of fluid collected by the drainage system; each of the at least one auxiliary collection chamber having an associated shut off valve.

11. The bodily fluid drainage system according to claim 1, wherein the mechanical volume limiting mechanism comprises:
   a central flotation member disposed inside the collection vessel; the inlet port of the collection vessel being defined in a top surface of the collection vessel; the central floatation member having an opening defined axially therethrough; a stopper head mounted on an upper surface of the central floatation member and aligned in an axial direction with the inlet port of the collection vessel;
   an axle mounted to a bottom surface of the collection vessel and extending axially upwards towards the top surface of the collection vessel; the axle passing through the opening defined in the central floatation member.

12. The bodily fluid drainage system according to claim 11, wherein a radial cross-section of the opening in the central floatation member and a radial cross-section of the axle are complementary and non-circular.

13. The bodily fluid drainage system according to claim 1, wherein the collection vessel is configured as a two-part telescopic design comprising an upper housing tubular section and a lower housing tubular section, each of the upper and lower housing tubular sections having an open end and an opposite closed end; the open end of the lower housing tubular section is nested within the open end of the upper housing section;
   complementary teeth are arranged on mating surfaces of the upper and lower housing sections, respectively, that are in physical contact with one another;
   an O-ring is disposed between the mating surfaces of the upper and lower housing sections;
   wherein volume capacity of the collection vessel is adjustable by axially displacing the lower housing tubular section relative to the upper housing tubular section.

14. The bodily fluid drainage system according to claim 1, wherein the volume limiting mechanism comprises:
   a flexible tubing having a secured end and an opposite free terminating end; the secured end of the flexible tubing being inserted into the inlet port of the collection vessel defined in a top surface of the collection vessel; while the free terminating end of the flexible tubing extends into the collection vessel; fluid passes through a lumen defined axially through the flexible tubing; a flotation member is disposed about the free terminating end of the flexible tubing; the floatation member rises axially simultaneously with fluid level of bodily fluid accumulated in the collection vessel; at some point with the rise of the floatation member, the flexible tubing will bend forming a kink that tapers the flow of bodily fluid therethrough; the bend in the flexible tubing eventually forming an angle ≤90° cutting off all flow of fluid therethrough.

* * * * *